US008591917B2

(12) United States Patent
Molina et al.

(10) Patent No.: US 8,591,917 B2
(45) Date of Patent: Nov. 26, 2013

(54) GANGLIOSIDE BASED VACCINE COMPOSITIONS FOR SUBCUTANEOUS ADMINISTRATION

(75) Inventors: Luis Enrique Fernández Molina, Ciudad de la Habana (CU); Circe Mesa Pardillo, Ciudad de la Habana (CU)

(73) Assignee: Centro de Inmunologia Molecular (CIM) (CU)

( * ) Notice: Subject to any disclaimer, the term of this patent is extended or adjusted under 35 U.S.C. 154(b) by 1066 days.

(21) Appl. No.: 10/547,164

(22) PCT Filed: Feb. 27, 2004

(86) PCT No.: PCT/CU2004/000003
§ 371 (c)(1),
(2), (4) Date: Jan. 23, 2007

(87) PCT Pub. No.: WO2004/075811
PCT Pub. Date: Sep. 10, 2004

(65) Prior Publication Data
US 2007/0148181 A1    Jun. 28, 2007

(30) Foreign Application Priority Data
Feb. 27, 2003    (CU) ...................................... 47-2003

(51) Int. Cl.
*A61K 39/02* (2006.01)
*A61K 39/095* (2006.01)
*C12Q 1/70* (2006.01)

(52) U.S. Cl.
USPC .......................... 424/234.1; 435/5; 424/250.1

(58) Field of Classification Search
None
See application file for complete search history.

(56) References Cited

U.S. PATENT DOCUMENTS 6,149,921 A * 11/2000 Rodriguez et al. ......... 424/277.1
2002/0136735 A1 * 9/2002 Molina et al. .............. 424/190.1

* cited by examiner

*Primary Examiner* — Benjamin P Blumel
(74) *Attorney, Agent, or Firm* — Lackenbach Siegel, LLP

(57) ABSTRACT

Vaccine compositions in which gangliosides and the OMP of *N. meningitidis* were combined to form very small size proteoliposomes (VSSP) to be administered subcutaneously are described, these compositions do not require the use of any additional adjuvant.

The described compositions allow the immunological treatments with gangliosides, particularly N-AcGM3/VSSP and N-GcGM3/VSSP, showing advantages due to the less aggressive reaction in the site of injection and can be used in a simpler way and better for the patients.

15 Claims, 2 Drawing Sheets

GANGLIOSIDE BASED VACCINE COMPOSITIONS FOR SUBCUTANEOUS ADMINISTRATION

PRIOR RELATED APPLICATIONS

This application claims priority to Cuban Patent Application CU47-2003, filed Feb. 27, 2003 and PCT Patent Application PCT/CU04/00003, filed Feb. 27, 2004 and incorporates by reference in their entireties thereto.

BACKGROUND OF THE INVENTION

1. Field of the Invention

The current invention is referred to vaccine compositions for subcutaneous administration containing gangliosides useful for the immunological treatment of autoimmune diseases, infectious diseases and tumors, without any additional adjuvant.

2. Background of the Prior Art

For a long time it is known the intention of using as immunological treatment of autoimmune diseases and cancer, for instance the U.S. Pat. No. 4,965,198 patent describes the use of ganglioside GM2 in the prevention and therapy of such diseases. In the filed patent EP-A-661061 and in the U.S. Pat. No. 6,149,921, vaccine compositions are described in order to stimulate or increase the antibody response against a ganglioside which consists in an immunogen and an immunological adjuvant.

The described immunogens are: VSSP (very small size proteoliposomes) constituted by the association of N-AcetylGM3 and N-GlycolylGM3 gangliosides from now on: (N-AcGM3) and (N-GcGM3), with the outer membrane protein complex (OMP) from *Neisseria meningitidis*.

Such immunogens from now on will be denominated N-AcGM3/VSSP and N-GcGM3/VSSP; they are very small size and practically invisible to the Electronic Microscope, water soluble and with increased floating capacity.

For the vaccine compositions described in EP-A-661061 and U.S. Pat. No. 6,149,921 the utilization of an adjuvant, such as the very well known Freund incomplete adjuvant, was required.

In the filed patent WO-A-02145746 vaccine compositions are described containing (A) one or more antigens with low immunogenicity; (B) VSSP with incorporated gangliosides mainly N-AcGM3/VSSP and N-GcGM3/VSSP; and (C) eventually one or more adjuvants.

In the paper of Carr A. et al., published in *Melanoma Research*, 2001, Vol. 11, pp 219-227, the anti-tumor activity of a vaccine containing N-AcGM3 ganglioside in mice bearing melanoma B16 is described.

In that article the influence of the presence of an immunological adjuvant, especially the complete Freund's adjuvant or the incomplete Freund's like adjuvant Montanide ISA 51, is also studied. The vaccines were administered intramuscularly and the emerging conclusion is that mice immunized with N-AcGM3/VSSP, with any of the adjuvants, Freund or Montanide ISA 51, showed IgM and IgG anti-N-AcGM3 responses at week $8^{th}$ (Table 1). In contrast, the N-AcGM3/VSSP vaccine without any adjuvant did not show any immunogenic response (page 223, right column).

Therefore, the state of the art teaches that vaccines containing VSSP conjugated with gangliosides should be formulated with adjuvants, mainly the Freund's (complete or incomplete) or Montanide ISA 51.

However, it is very well known that when they are parentherally administered, such adjuvants, particularly the Freund's complete adjuvant, provoke some inconvenient side effects such as chronic inflammation in the injection site, eventual granulomas and sterile abscess or ulcerative necrosis in tissues. Montanide ISA 51 is less aggressive but also can cause some inflammatory disorders.

It would be very desirable from the point of view of their applications in the immunological treatments of autoimmune, infectious and tumoral diseases to have new gangliosides vaccine compositions which are less aggressive in the injection site and that could be more easily used with less inconvenient for the patients.

The authors of the present invention have discovered that the ganglioside based vaccines formulated with VSSP, when administered subcutaneously can be used without any adjuvants while there still be present the relevant immunological properties.

The aims of the present invention are new vaccine compositions included in VSSP, preferably N-AcGM3/VSSP and N-GcGM3/VSSP, which do not contain any immunological adjuvant and are administered subcutaneously.

Is also an objective of the present invention a method for the treatment of a patient who required a reinforcement of their immunological response consisting in the subcutaneous administration of the ganglioside vaccine compositions, preferably N-AcGM3/VSSP and N-GcGM3/VSSP, which do not contain any immunological adjuvant.

Is also the objective of the present invention N-AcGM3/VSSP and/or N-GcGM3/VSSP vaccine compositions not containing other antigenic components different from gangliosides or any other immunological adjuvants and are administered subcutaneously.

DESCRIPTION OF THE INVENTION

The vaccine compositions objectives of the present invention consist in the dissolution or aqueous dispersion of one or more gangliosides and their inclusion into the OMP of the *N. meningitidis* (VSSP), capable of stimulate the immunological response by subcutaneous administration without any additional immunological adjuvant.

VSSP are highly stable ganglioside hydrophobic associations with the outer membrane protein complex of *Neisseria meningitidis*, without the necessity of covalent links. Such gangliosides-proteins systems are described in detail in patents EP-A-661061 and U.S. Pat. No. 6,149,921, and also in different publications for instance, Estévez et al. *Vaccine*, 1999; Vol. 18(1-2): pp 190-197. In such documents the procedure for obtaining them is also described.

Among the gangliosides included in VSSP results a preference of the present invention the N-AcGM3 and N-GcGM3, being specially preferred the N-AcGM3.

A detailed description of the immunogenicity of both conjugated gangliosides as well as their application as anticancer agents and stimulants of the acquired immunity can be found in the above mentioned documents and in the review article: Bitton R. Et al., *Oncology Reports* (2002), Vol 9, pp 267-276, and in recent communications and scientific meetings for instance The $6^{th}$ Latin-American Congress of Immunology which took place in Havana on Dec. 9, 2002, communication of Sáurez G. et al. *"Phase I clinical trial of the ganglioside cancer vaccine N-Acetil-GM3/VSSP/Montanide ISA 51 in advanced breast cancer patients"*.

The vaccine compositions not containing other antigenic components than gangliosides are the preferred object of the invention being specially preferred those containing as unique immunogenic component N-AcGM3 (N-AcGM3/

VSSP) and or N-GcGM3 (N-GcGM3/VSSP), being specially preferred those containing only N-AcGM3/VSSP.

The vaccine compositions object of the present invention are solutions or aqueous dispersion of the VSSP which can eventually contain other non-toxic, non-irritant water-compatible dissolvents normally used in pharmaceuticals for parentheral use as could be polyethylenglycol.

The conjugated ganglioside concentration in the solutions or aqueous dispersions is not critic and can be in the range 0.03%-3% (w/v), preferably between 0.04% and 2.5% (w/v). The range of SC administered doses, used for the referred vaccines in the present invention, is between 50 μg and 2.4 mg, preferably between 200 μg and 2 mg.

An essential characteristic of the vaccine compositions, object of this invention, is that they are designed to be administered subcutaneously without any additional immunological adjuvant.

Immunological adjuvants are frequently used in vaccine formulations. Such adjuvants favored the immunogenic action in different ways:

Creating an antigen deposit in the injection site liberating or releasing the antigen in a systematic form.

Helping the antigen to reach the spleen and the lymph nodes through the formation of oily micro drops easily trapped by the macrophages Activating directly or indirectly the cells involved in the immune response.

Most known immunological adjuvants are: Freund's, complete and incomplete, Montanide ISA, Ribi adjuvants, Hunter's TiterMax, Aluminum salts, Gerbu adjuvant, QS-21, etc.

Surprisingly and unexpectedly the authors of the present invention have found that when gangliosidesNSSP vaccines are administered SC the adjuvants can be completely eliminated. This was, in spite of the previous state of the art, excluded almost completely for the intramuscular administration.

Therefore the present invention represents undeniable advantages almost all when concerns the referred inflammatory problems locally derived from the use of adjuvants. This is a method of vaccination with gangliosides simple, with efficacy and less aggressive for the patients.

In the following examples the comparative experimental details is included allowing to demonstrate the immunological efficacy of the vaccine composition without containing immunological adjuvants.

Example 1

Using the procedure described in example 3 of U.S. Pat. No. 6,149,921 patent an aqueous vaccine composition was prepared (buffer Tris-HCl) containing 2.4 mg/mL of N-AcGM3/VSSP. To an aliquot of such immunogen composition the same volume of Montanide ISA 51 adjuvant was added (Seppic Paris, France). At the same time to another aliquot an identical volume of buffer Tris-HCl was added.

Two vaccine compositions were obtained:
A: Aqueous solution containing 1.2 mg/mL N-AcGM3/VSSP.
B: Emulsion W/O containing 1.2 mg/mL N-AcGM3/VSSP.

50 C57BL/6 female mice were selected with a body weight between 18-20 g, and organized in 5 experimental groups of 10 animals each.

Group 1 (control) animals were inoculated intramuscularly, at days 0, 14, 28 and 42, with 0.1 mL of phosphate buffer saline (PBS).

Group 2 animals were inoculated intramuscularly, at days 0, 14, 28 and 42, with 0.1 mL of vaccine composition B (120 μg of N-AcGM3/VSSP).

Group 3 (control) animals were inoculated subcutaneously, at days 0, 14, 28 and 42, with 0.1 mL (PBS).

Group 4 animals were inoculated subcutaneously, at days 0, 14, 28 and 42, with 0.1 mL of vaccine composition B (120 μg of N-AcGM3/VSSP).

Group 5 animals were inoculated subcutaneously, at days 0, 14, 28 and 42, with 0.1 mL vaccine composition A (120 μg of N-AcGM3/VSSP).

Mice in all Groups were challenged on day 63 with $5 \times 10^3$ cells of melanoma MB16F10 subcutaneously (0.2 mL).

The animals were individualized since day 0 and the following parameters were determined twice a week: tumor volume, survival, and time to progression.

The results obtained were the following:

Tumor Volume:

In FIG. 1, tumor growth kinetic from each experimental group is shown. Mann-Whitney (two-tailed) U test was used to assess the statistical significance in the paired groups of tumor volumes values from individualized animals on day 33rd after the tumor challenge.

This statistical method is especially appropriate for the evaluation of this kind of experiments in which there is a natural dispersion of data related to a biologic event.

The p value represent the probability associated with the practical value calculated from the sample and allows to define the nearness of the Alfa value (significance) calculated by the stadigraph and the actual data validating the nule hypothesis ($p > 0.05$)

Results are shown in FIG. 1 and Table 1

TABLE 1

Effect of vaccination on tumoral volume

| Groups | Tumor Volume ($cm^3$) Day 33 | |
|---|---|---|
| | Mean | Mann-Whitney U p values (Two-tailed) |
| Group 1 | 6.53 | — |
| Group 2 | 3.99 | $0.46^a$ |
| Group 3 | 6.63 | — |
| Group 4 | 4.11 | $0.12^b$ |
| Group 5 | 1.89 | $0.01^c$ |

[a] p value as result of the comparison of Group 2 vs. Group 1
[b] p value as result of the comparison of Group 4 vs. Group 3
[c] p value as result of the comparison of Group 5 vs Group 3

From FIG. 1 and Table 1 it can be seen that mice in Group 5, vaccinated subcutaneously with a composition object of the present invention, show a significant decrease in the tumoral volume in relation to the other groups in the experiment and the corresponding controls.

Survival

This parameter evaluates the capacity of vaccination to increase the life span of the immunized animals for a tumor as lethal as the MB16. The parameter is measured in days comparing with the survival in the non treated animals. For statistic significance is used the Log-Rank test.

Obtained values are shown in FIG. 2 and Table 2. In Table 2 the phrase reference group X means the group which is compared with each column.

TABLE 2

Statistic of survival time according to Log-Rank test

| Groups | Survival (days) media | Survival (days) median | p (reference Group 1) | p (reference Group 3) | p (reference Group 5) |
|---|---|---|---|---|---|
| Group 1 | 35 | 33 | — | — | — |
| Group 2 | 43 | 36 | 0.06 | — | 0.26 |
| Group 3 | 40 | 40 | — | — | 0.002 |
| Group 4 | 42 | 40 | — | 0.53 | 0.13 |
| Group 5 | 52 | 53 | — | 0.002 | — |

These results demonstrated that mice included in Group 5, SC vaccinated with the formulation object of the present invention showed the longest survival after the inoculation of the tumor.

Time to Progression

Time to progression is a parameter that evaluates the period that takes a tumor to be evident in each animal individually, measured since the moment of the inoculation. In table 3 the results are shown:

TABLE 3

Statistics of the time to progression according to the Log-Rank Test.

| Groups | Time to progression (days) media | Time to progression (days) median | p (reference group1) | p (reference group 3) | p (reference group 5) |
|---|---|---|---|---|---|
| Group 1 | 19 | 19 | — | — | — |
| Group 2 | 32 | 19 | 0.02 | — | 0.5 |
| Group 3 | 19 | 19 | — | — | 0.004 |
| Group 4 | 23 | 19 | — | 0.5 | 0.06 |
| Group 5 | 37 | 26 | — | 0.004 | — |

For mice which had not developed any tumor at the time of finishing the experiment the progression was considered as 60 days The impact in prolonging the time to progression is obviously a parameter very desired to obtain significant differences in a vaccine against cancer and according to the results observed in Table 3 the animals of Group 5, SC vaccinated with the VSSP composition object of the present invention, showed the more relevant positive results.

Tumor Regression

In Groups 4 and 5, corresponding to subcutaneous vaccination with and without adjuvant, an animal with tumor regression was observed. In the animal of Group 4 the tumor was measurable at day 19th of the inoculation keeping practically without any growth until day 35 which was found negative. The mouse of Group 5 showed the presence of tumor by palpation on day 26 of inoculation and was reported as negative on day $29^{th}$.

Overall Evaluation

The results of the experiments showed that the vaccine composition object of this invention increased the survival time and the time to progression, at the same time decreasing the tumoral growth speed in a significant way in relation to the control group treated with PBS.

On the other hand, the administration of a vaccine composition containing the adjuvant Montanide ISA 51 only protected when administered intramuscularly showing total inefficacy when administered subcutaneously.

BRIEF SUMMARY OF THE INVENTION

In summary, the subcutaneous vaccination with the vaccine compositions object of this invention showed superior results in relation to the results obtained with the intramuscular way with the vaccine compositions containing an adjuvant of the Montanide type.

Figure 1:
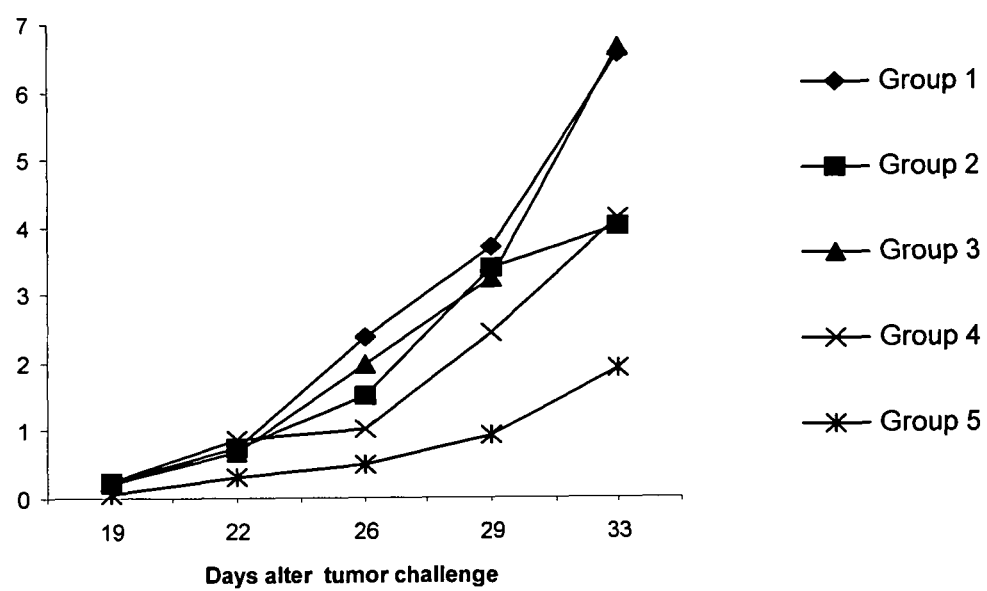
FIG. 1 represents a graphic showing the evolution of the tumor volume in 5 Groups of animals submitted to different vaccine treatments and challenged with malignant tumors.
Figure 2:
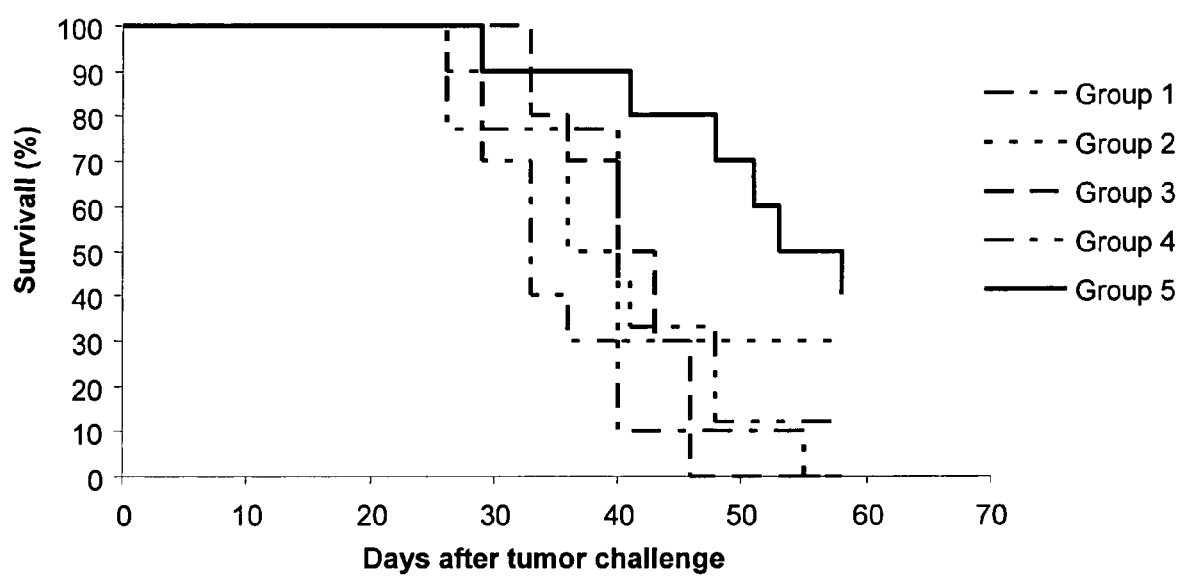
FIG. 2 represents a graphic which allows appreciating the survival parameter in the 5 Groups of experimental animals.

The invention claimed is:

1. An adjuvant-free subcutaneously administrable vaccine composition, comprising a solution or aqueous dispersion of at least one ganglioside selected from the group consisting of: N-AcGM3 or N-GcGM3.

2. The composition of claim 1, wherein the ganglioside is N-GcGM3.

3. The composition of claim 1, wherein the ganglioside is N-AcGM3.

4. The composition of claim 1, wherein the composition does not contain other antigens different from said ganglioside(s).

5. The composition of claim 1, further comprising immunological components N-AcGM3/VSSP and for N-GcGM3/VSSP.

6. The composition of claim 5, wherein the immunological component is N-AcGM3/VSSP.

7. A method for stimulating an immune response in a patient or subject, comprising; providing a composition comprising a solution or aqueous dispersion of at least one ganglioside selected from the group consisting of: N-AcGM3 or N-GcGM3, said composition being free of adjuvant, and subcutaneously administering the composition to the patient or subject.

8. The composition of claim 5, wherein the immunological component is N-GcGM3/VSSP.

9. The method of claim 7, wherein the ganglioside is N-AcGM3.

10. An adjuvant-free subcutaneously administrable composition, said composition comprising at least one ganglioside selected from the group consisting of: N-AcGM3 or N-GcGM3 and being free of adjuvant and wherein the composition does not contain other antigens different from said ganglioside.

11. The method of claim 7, wherein the ganglioside is N-GcGM3.

12. The method of claim 7, wherein the composition does not contain other antigens different from said ganglioside(s).

13. The method of claim 7, further comprising immunological components N-AcGM3/VSSP and/or N-GcGM3/VSSP.

14. The method of claim 13, wherein the immunological component is N-AcGM3/VSSP.

15. The method of claim 13, wherein the immunological component is N-GcGM3/VSSP.

* * * * *